United States Patent [19]
Weber et al.

[11] Patent Number: 5,174,996
[45] Date of Patent: Dec. 29, 1992

[54] NAIL ENAMEL CONTAINING OXIDIZED POLYETHYLENE COATED INORGANIC PIGMENTS

[75] Inventors: Robert A. Weber, Suffern, N.Y.; Christopher C. Frankfurt, Old Bridge; A. John Penicnak, Mountain Lakes, both of N.J.

[73] Assignee: L'Oreal S.A., Paris, France

[21] Appl. No.: 824,714

[22] Filed: Jan. 17, 1992

Related U.S. Application Data

[63] Continuation of Ser. No. 591,297, Oct. 1, 1990, abandoned.

[51] Int. Cl.$^5$ .......................... A61K 6/00; A61K 7/04
[52] U.S. Cl. ........................................ 424/401; 424/61
[58] Field of Search ................................ 424/61, 401

[56] References Cited

U.S. PATENT DOCUMENTS

| | | | |
|---|---|---|---|
| 3,864,294 | 2/1975 | Busch, Jr. | 424/61 |
| 4,832,944 | 5/1989 | Socci et al. | 424/613 |
| 4,919,922 | 8/1989 | Miyoshi et al. | 424/63 |

OTHER PUBLICATIONS

*Cosmetics, Science and Technology*, 2nd Edition, vol. 2, Chapter 29.

Primary Examiner—Thurman K. Page
Assistant Examiner—D. Gabrielle Phelan
Attorney, Agent, or Firm—Brumbaugh, Graves, Donohue & Raymond

[57] ABSTRACT

Nail enamels of improved quality as regards settling, migration and flotation characteristics are provided by utilizing therein pigments coated with oxidized polyethylene.

5 Claims, No Drawings

NAIL ENAMEL CONTAINING OXIDIZED POLYETHYLENE COATED INORGANIC PIGMENTS

This application is a continuation of Ser. No. 07/591,297, filed Oct. 1, 1990, now abandoned.

BACKGROUND OF THE INVENTION

The present invention relates to a nail enamel or lacquer. The invention particularly relates to nail enamels which are not only substantially free of settling and migration of the pigment and other materials suspended in a composition but are also substantially reduced or free from the flotation problem often found with nail enamels.

U.S. Pat. No. 4,832,944 addresses the problem of preventing the settling and migration of pigments and other materials suspended in nail enamels. According to the patent, this is accomplished by utilizing inorganic pigments having a coating thereon consisting of organically substituted polysiloxanes which are chemically bonded to the pigment surface. Applicants have observed that the use of polysiloxane coated inorganic pigments does in fact substantially reduce the problems of pigment migration and settling. However, use of the polysiloxane coated pigments does not provide protection against the undesirable phenomenon known as flotation, a problem which is characterized by the appearance of a layer of clear liquid on the top of a bottle of nail enamel after a period of storage. The clear material does not contain pigments and thus must be reincorporated into the rest of the enamel by stirring or shaking before the enamel is used. This, of course, is undesirable.

BRIEF SUMMARY OF INVENTION

It has now been found that a nail enamel of greatly improved settling and migration characteristics and which is substantially free from the flotation problem is provided by formulating a nail enamel which contains an inorganic pigment that has been coated with oxidized polyethylene.

DETAILED DESCRIPTION OF THE INVENTION

The inorganic pigments which are useful in accordance with this invention are conventional nail enamel pigments which have been coated with oxidized polyethylene. One suitable source of such coated materials is the U.S. Cosmetics Corporation of Dayville, Conn. While the pigment can be supplied with levels of polyethylene treatment ranging from 1% to 10% by weight, a level in the range of from 1% to 4%, preferably 3% applied to the surface of the pigment has been found to provide good results.

Examples of such pigments include iron oxides, titanium dioxide, titanated mica, iron oxide coated mica, ultramarine, chromium oxide, chromium hydroxide, manganese violet, and any other suitable recognized prior art pigment. Preferred among these are the iron oxide and titanium dioxide pigments.

In addition to the coated pigment, the nail enamel contains an otherwise conventional base including nitrocellulose, solvent, modifying resin, plasticizer, and suspending agent, and the nail enamels are prepared by conventional procedures. Examples of suitable enamel bases and procedures for preparing them are found in *Cosmetics, Science and Technology*, Edited by Balsam and Sagarin. 2nd Edition, Vol. 2, Chapter 29 (Wiley Interscience, New York, N.Y.).

The coated pigment is dispersed into the other nail enamel components by conventional techniques employed in nail enamel manufacture such as roller milling and chipping.

The table given in the Examples illustrates formulations that may be used and the differences between polyethylene treated, polysiloxane treated, and untreated inorganic pigments. Where the pigment is indicated as polyethylene treated, it has been coated with oxidized polyethylene and is available from U.S. Cosmetics, Connecticut as product number PI-T-3328 for the titanium dioxide and PT-C33-8075 and PT-B-335198 for the iron oxides. The pigment labelled polysiloxane treated is coated with poly(methylhydrogen) siloxane and was obtained from Clark Colors as product number 9454 for the coated iron oxides and product number 9428 for the coated titanium dioxide.

The numerical flotation evaluation ratings given in the table has the following meaning for stability:

| | | |
|---|---|---|
| 1. | Excellent | No visible sign of flotation. |
| 2. | Good | Very slight flotation. |
| 3. | Average | Some flotation. |
| 4. | Poor | Flotation readily apparent. |
| 5. | Unacceptable | Very bad flotation. |

The numerical evaluation ratings for migration and settling have the following meanings:

| | | |
|---|---|---|
| 1. | Excellent | No migration or settling. |
| 2. | Good | Very slight settling; no migration. |
| 3. | Average | Some settling; very slight migration. |
| 4. | Poor | Settling and migration readily apparent. |
| 5. | Unacceptable | Product not saleable |

EXAMPLE

Three samples of a nail enamel ("Whimsy Pink") were prepared by uniformly mixing the ingredients given in the table below. The amounts are by weight. The products were compared for settling, migration, and flotation after 4 months storage without agitation at room temperature and at 45° C. Both polyethylene and polysiloxane are present on the treated pigment at a level of 3% by weight.

| Sample No. | 1 | 2 | 3 |
|---|---|---|---|
| n-Butyl Acetate | 25.00 | 25.00 | 25.00 |
| Toluene | 25.00 | 25.00 | 25.00 |
| Ethyl Acetate | 10.00 | 10.00 | 10.00 |
| Isopropyl Alcohol | 6.75 | 6.75 | 6.75 |
| Bentone 27 (montmorillonite) | 1.00 | 1.00 | 1.00 |
| Nitrocellulose | 16.00 | 16.00 | 16.00 |
| Toluenesulfonamide formaldehyde resin | 9.00 | 9.00 | 9.00 |
| Dibutyl phthalate | 5.00 | 5.00 | 5.00 |
| Camphor | 1.00 | 1.00 | 1.00 |
| Titanium dioxide (polyethylene) | 1.00 | — | — |
| Titanium dioxide (polysiloxane) | — | 1.00 | — |
| Titanium dioxide (untreated) | — | — | 1.00 |
| Iron oxide, black (polyethylene) | 0.10 | — | — |
| Iron oxide, black (polysiloxane) | — | 0.10 | — |
| Iron oxide, black (untreated) | — | — | 0.10 |
| Iron oxide, russet (polyethylene) | 0.05 | — | — |
| Iron oxide, russet (polysiloxane) | — | 0.05 | — |

-continued

| Sample No. | 1 | 2 | 3 |
|---|---|---|---|
| Iron oxide, russet (untreated) | — | — | 0.05 |
| D & C Red No. 6, barium lake (untreated) | 0.10 | 0.10 | 0.10 |
| Flotation observation after 4 mos. | | | |
| Room Temperature | 1 | 2 | 1 |
| 45° C. | 2 | 3 | 2 |
| Settling, migration after 4 mos. | | | |
| Room Temperature | 1 | 1 | 3 |
| 45° C. | 1 | 1 | 4 |

As can be seen from the results of this work, polysiloxane treatment (Sample No. 2) provides a good product which has no settling or migration of enamel ingredients on a 4-month storage period, both at room temperature and at 45° C. However, these products did not perform well in the flotation test, being evaluated at a 2 level at room temperature and at a 3 level at 45° C. The product of the present invention (Sample No. 1), in contrast, performed very well in the flotation test, as well as in the settling and migration tests.

Definitions

For the purpose of the present invention, the following terms are defined:

settling—describes the problem noted in nail enamels when solids, including pigments, accumulate on the bottom of a bottle of nail enamel.

migration—pigments in nail enamel form striations, marbleization and/or layering effects, leading to non-uniform appearance.

flotation—this term describes the phenomenon where a clear liquid collects at the top of the nail enamel bottle.

We claim:

1. A nail enamel comprising at least one film-forming material, at least one plasticizer, at least one solvent for the film-forming material and plasticizer and at least one inorganic pigment, the inorganic pigment being one which has been coated with 1% to 10% by weight oxidized polyethylene to form an adsorbed coating on the pigment particles.

2. The nail enamel of claim 1, wherein the inorganic pigment is selected from the group consisting of iron oxides, titanated mica, titanium dioxide, ultramarine, chromium oxide, chromium hydroxide and manganese violet.

3. In a method of preparing nail enamel containing at least one film-forming material, at least one plasticizer, at least one solvent for the film-forming material and the plasticizer, and at least one inorganic pigment, the improvement comprising the step of dispersing an inorganic pigment having 1% to 10% by weight oxidized polyethylene adsorbed onto the surface of said inorganic pigment in the mixture of the film-forming material, plasticizer and solvent.

4. In a method of preparing nail enamel containing at least one film-forming material, at least one plasticizer, at least one solvent for the film-forming materials and the plasticizer, and at least one inorganic pigment selected from the group consisting of iron oxides, titanated mica, titanium dioxide, ultramarine, chromium oxide, chromium hydroxide and manganese violet, the improvement comprising the step of utilizing an inorganic pigment having a surface treatment of oxidized polyethylene and dispensing said coated pigment particles in a mixture of the film-forming material, plasticizer and solvent, the pigment being coated to have 1–10% by weight of oxidized polyethylene adsorbed on the surface of the pigment particles.

5. The method of claim 4, wherein the inorganic pigment is titanium dioxide.

* * * * *